United States Patent [19]

Coates et al.

[11] 4,082,843
[45] * Apr. 4, 1978

[54] 3-(3-(3-SUBSTITUTED AMINO-2-HYDROXYPROPOXY)PHENYL)-6-HYDRAZINO PYRIDAZINES AND THEIR USE AS VASODILATORS AND β-ADRENERGIC BLOCKING AGENTS

[75] Inventors: William John Coates, Welwyn Garden City; Anthony Maitland Roe, Hatfield; Robert Antony Slater, Letchworth; Edwin Michael Taylor, Welwyn, all of England

[73] Assignee: Smith Kline & French Laboratories Limited, Welwyn Garden City, England

[ * ] Notice: The portion of the term of this patent subsequent to Oct. 11, 1994, has been disclaimed.

[21] Appl. No.: 640,666

[22] Filed: Dec. 15, 1975

Related U.S. Application Data

[63] Continuation of Ser. No. 635,476, Nov. 26, 1975, abandoned.

[51] Int. Cl.$^2$ .................. C07D 237/20; A61K 31/50
[52] U.S. Cl. .................. 424/250; 260/250 A; 260/519; 260/521 H
[58] Field of Search .................. 260/250 A; 424/250

[56] References Cited

U.S. PATENT DOCUMENTS

| 3,769,278 | 10/1973 | Heri | 424/250 |
| 3,818,097 | 6/1974 | Black et al. | 424/273 |
| 3,881,015 | 4/1975 | Black | 424/273 |
| 3,931,177 | 1/1976 | Coates et al. | 260/250 A |
| 3,975,530 | 8/1976 | Durant et al. | 424/270 |
| 4,011,321 | 3/1977 | Coates | 424/250 |

Primary Examiner—Donald G. Daus
Assistant Examiner—Mark L. Berch
Attorney, Agent, or Firm—Joan S. Keps; Richard D. Foggio; William H. Edgerton

[57] ABSTRACT

The compounds are 3-(3-(3-substituted amino-2-hydroxypropoxy)phenyl)-6-hydrazino pyridazines which have β-adrenergic blocking and vasodilator activity.

12 Claims, No Drawings

3-(3-(3-SUBSTITUTED AMINO-2-HYDROXYPROPOXY)PHENYL)-6-HYDRAZINO PYRIDAZINES AND THEIR USE AS VASODILATORS AND β-ADRENERGIC BLOCKING AGENTS

This application is a continuation of Ser. No. 635,476 filed Nov. 26, 1975, now abandoned.

This invention relates to pharmacologically active compounds and in particular to certain substituted phenyl hydrazinopyridazines which have β-adrenergic blocking and vasodilator activity. This invention also relates to processes for the production of said compounds, to pharmaceutical compositions comprising them and to methods of treatment employing their use.

The compounds of the present invention are represented by the following Formula I

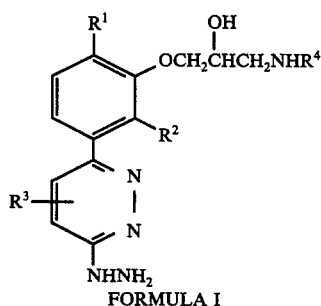

wherein $R^1$ or $R^2$ is hydrogen, the other group being hydrogen, methyl, fluoro, chloro, bromo, hydroxy, methoxy, hydroxymethyl, cyano, nitro or amino;

$R^3$ is hydrogen or methyl; and $R^4$ is isopropyl, tertiary butyl or phenylethyl; and pharmaceutically acceptable acid addition salts thereof.

Preferably $R^1$ or $R^2$ is hydrogen, the other group being hydrogen, methyl, fluoro, chloro, hydroxy, methoxy or cyano.

In a preferred group of compounds $R^2$ is hydrogen and $R^1$ is methyl, fluoro, methoxy or cyano.

In another preferred group of compounds $R^1$ is hydrogen and $R^2$ is fluoro, chloro or cyano. Preferably $R^4$ is isopropyl or tertiary butyl. Examples of preferred compounds which fall within the scope of the present invention are:

3-[3-(3-t-butylamino-2-hydroxypropoxy)phenyl]-6-hydrazinopyridazine

3-[3-(3-t-butylamino-2-hydroxypropoxy)-4-methylphenyl]-6-hydrazinopyridazine

3-[3-(3-t-butylamino-2-hydroxypropoxy)-4-cyanophenyl]-6-hydrazinopyridazine

3-[3-(3-t-butylamino-2-hydroxypropoxy)-4-fluorophenyl]-6-hydrazinopyridazine

The compounds of this invention exist as optical isomers and the S-absolute configuration is preferred. Racemic mixtures of the compounds of Formula I can be resolved by conventional methods, such as recrystallisation of salts formed with optically active acids, but preferably the intermediates of Formula 5 are resolved before conversion into hydrazinopyridazines.

The compounds of Formula I may be prepared by the processes outlined in Scheme 1. In the schemes $R^1$, $R^2$, $R^3$ and $R^4$ have the same significance as in Formula I or they may also be protected derivatives thereof of precursors thereof.

SCHEME I

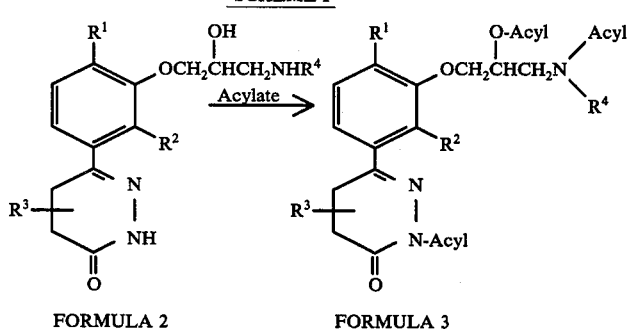

SCHEME I -continued

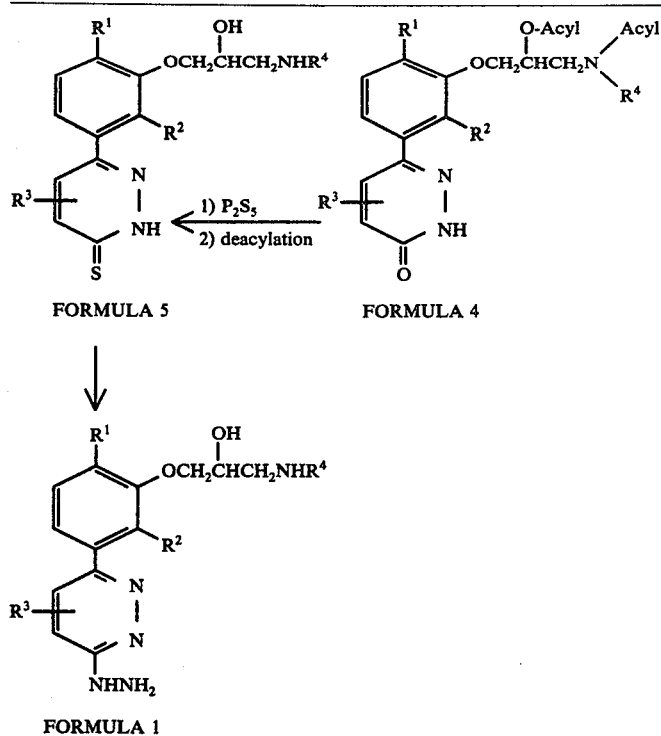

Acylation of a phenyl dihydropyridazinone of Formula 2, wherein $R^1$, $R^2$, $R^3$ and $R^4$ have the same significance as in Formula 1, gives a compound of Formula 3, wherein the hydroxy and amino groups of the side chain are protected. A suitable acyl group is the acetyl group which may be introduced by reaction of a compound of Formula 2 with acetic anhydride in the presence of a suitable base, e.g. pyridine or potassium acetate. Acetylation of the dihydropyridazonone ring also occurs, and this acetyl group is removed during subsequent bromination. Another suitable acyl group is the benzyloxycarbonyl group which may be introduced by treating a compound of Formula 2 with benzyl chloroformate under basic conditions. The triacylated compound of Formula 3 is dehydrogenated to give a phenylpyridazinone of Formula 4.

In many cases bromine in acetic acid is a suitable reagent for this dehydrogenation, and when the acyl group is acetyl it is preferred that the compound of Formula 3 is not isolated before treatment with bromine. Dehydrogenation of a compound of Formula 2 may also be achieved directly by the use of sodium 3-nitrobenzene sulphonate, chloranil or other similar dehydrogenating agents, and is followed by acylation to give a compound of Formula 4. Treatment of the phenylpyridazinone of Formula 4 with phosphorus pentasulphide in pyridine gives the corresponding thione (which may be obtained in mixture with the corresponding N-thioacylaminopropyl derivative) which is deacylated under suitable conditions to give the thione of Formula 5. The acetyl group may conveniently be removed using sodium hydroxide in methanol. Treatment of the thione of Formula 5 with hydrazine gives the required compound of Formula I.

The compounds of Formula 5 are referred to as thiones and are drawn as such, but these compounds may also exist in a tautomeric mercaptopyridazine form. Similarly the dihydropyridazinones of Formula 2 may exist as a tautomeric mixture with the corresponding hydroxypyridazines.

The intermediate phenyl dihydropyridazinones of Formula 2 may be prepared according to a reaction sequence shown in Scheme 2, wherein $R^1$, $R^2$, $R^3$ and $R^4$ have the same significance as in Formula I and one of $R^5$ and $R^6$ may be methyl and $R^7$ is hydroxy, amino or any other suitable group such as lower alkoxy or lower alkylamino, which can be displaced with hydrazine.

Many of the phenyldihydropyridazinones of Formula 2 are described and claimed inter alia in our co-pending British Application No. 58726/73.

Compounds of Formula 6 wherein $R^2$ is hydrogen and $R^1$ is hydrogen, methyl, fluoro, chloro, bromo or methoxy may be prepared by treating a corresponding compound of Formula 8 with succinic anhydride and a Lewis acid such as aluminium trichloride, and successively nitrating, reducing and diazotizing the major parasubstituted intermediate, and finally decomposing the diazonium derivative.

SCHEME 2

(X represents Chlorine or Bromine)

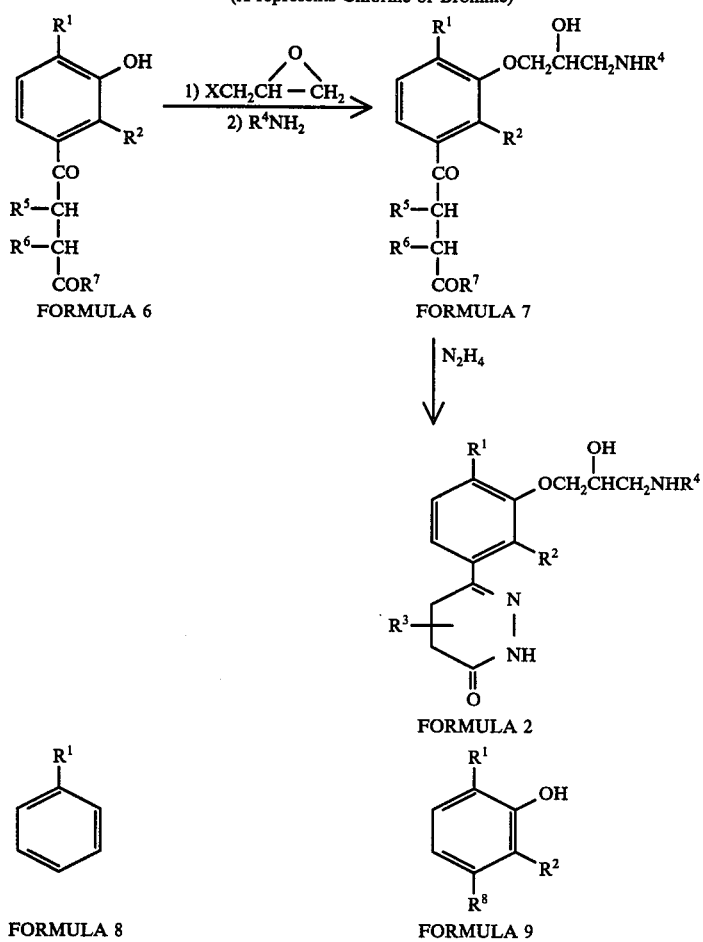

Compounds of Formula 6 wherein $R^2$ is methyl or methoxy may be prepared from the corresponding compounds of Formula 9 wherein $R^8$ is bromine or —COCH$_2$R$^3$. When $R^8$ is bromine the compound of Formula 9 may be converted into a Grignard reagent, aryllithium derivative or similar organometallic derivative which is subsequently treated with N-methylsuccinimide or similar compound. The hydroxyl group is protected during this reaction sequence, for example, by benzylation. In either of the above cases the succinic anhydride or N-methylsuccinimide may be substituted with a methyl group to give the appropriate compounds of Formula 6 wherein either $R^5$ or $R^6$ is methyl.

Compounds of Formula 6 wherein $R^1$ is hydrogen and $R^2$ is hydroxy may be prepared according to the following reaction scheme.

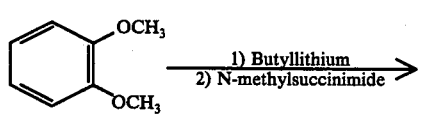

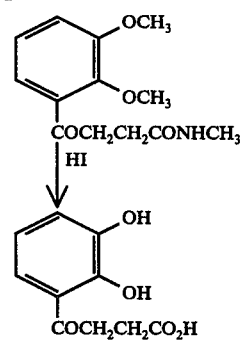

Compounds of Formula 6 wherein $R^1$ is hydrogen and $R^2$ is methyl, fluoro, chloro, or bromo may be prepared by the following reaction scheme.

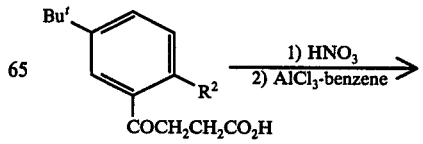

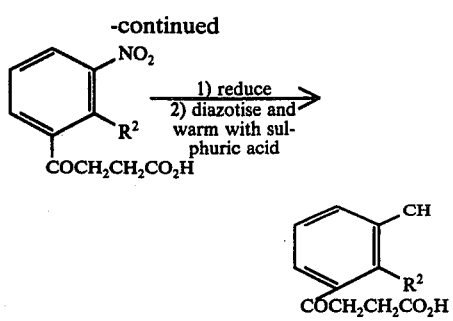

An alternative method for the production of compounds of Formula 6 is that wherein an aromatic aldehyde of Formula 10, for example that wherein $R^2$ is chlorine, is treated with sodium cyanide and acrylonitrile and the product hydrolysed under acidic conditions

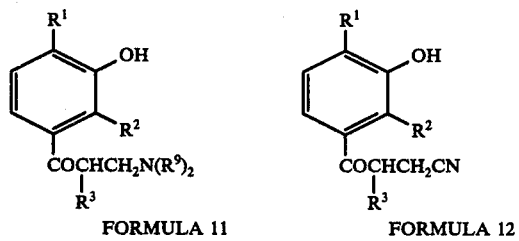

When $R^8$ is —$COCH_2R^3$, the phenol of Formula 9 may be treated with formaldehyde and a di-(lower alkyl) amine to give a compound of Formula 11 wherein $R^9$ is lower alkyl or $(R^9)_2$ is a polymethylene chain which forms a heterocyclic ring with the nitrogen atom shown. The compounds of Formula 11 may be alkylated to give the corresponding quaternary derivatives. The compounds of Formula 11 and the corresponding quaternary derivatives may be treated with an inorganic cyanide to give a nitrile of Formula 12. The phenol group may be protected, for example as the acetate ester, during these processes.

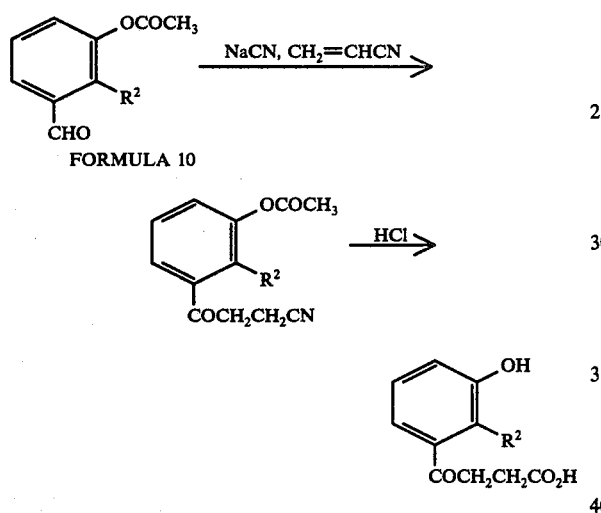

The compounds of Formula 6 may readily be obtained from the nitriles of Formula 12 e.g., by hydrolysis of the latter to the corresponding amides or carboxylic acids.

The compounds of Formula 6 are successively treated with epichlorohydrin or epibromohydrin, an amine $R^4NH_2$, and hydrazine to give the phenyldihydropyridazinones of Formula 2. Alternatively, the phenyldihydropyridazinones of Formula 2 may be prepared by first treating the compounds of Formula 6 to give the dihydropyridazinones of Formula 13 and then successively treating these compounds with epichlorohydrin or epibromohydrin, and then an amine $R^4NH_2$, as shown in Scheme 3. With the latter route alkylation of the dihydropyridazinone ring may occur.

SCHEME 3

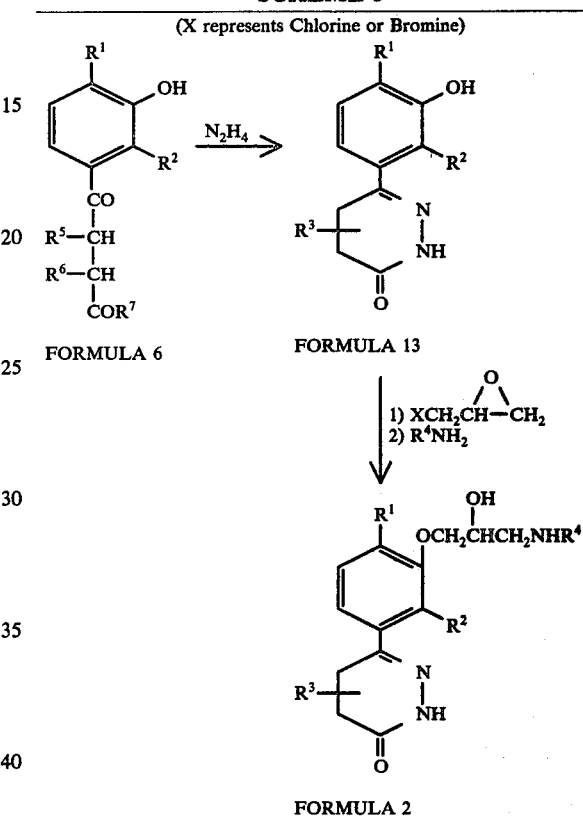

An alternative series of reactions is possible, wherein the various reactive groupings present in the compounds of our invention may be introduced at different stages from those illustrated in Scheme 1. One series, illustrated as Scheme 4, starts with the compound of Formula 13 and the additional double bond is first introduced into the 4,5- position of the pyridazinone ring by dehydrogenation under conditions mentioned above as being suitable for the dehydrogenation of the compounds of Formula 3. The phenolic group is then protected with a suitable protecting group, such as the ethoxycarbonyl group which may be introduced using ethyl chloroformate. The 3-oxo substituent of the pyridazine ring is converted into a 3-hydrazino group by treatment with phsophoryl chloride or phosphorous pentasulphide, removal of the phenolic protecting group and treatment of the product with hydrazine or an alkoxide of phenoxide followed by hydrazine. For example, the ethoxycarbonyl protecting group may be removed under mild basic conditions. The hydrazino group is then protected by reacting it with an alkoxycarbonyl halide, a ketone or an aldehyde, and the 3-alkylamino-2-hydroxy-1-propoxy side chain is introduced by successive reaction with epichlorohydrin or epibromohydrin and an amine R⁴NH₂. Removal of the protecting group on the hydrazino group (e.g. with acid) finally yields the required compounds of Formula 1.

In all the series of reactions described the hydrazino group may be introduced by reaction with hydrazine or a suitable protected derivative thereof, such as t-butyl carbazate or a hydrazone.

SCHEME 4

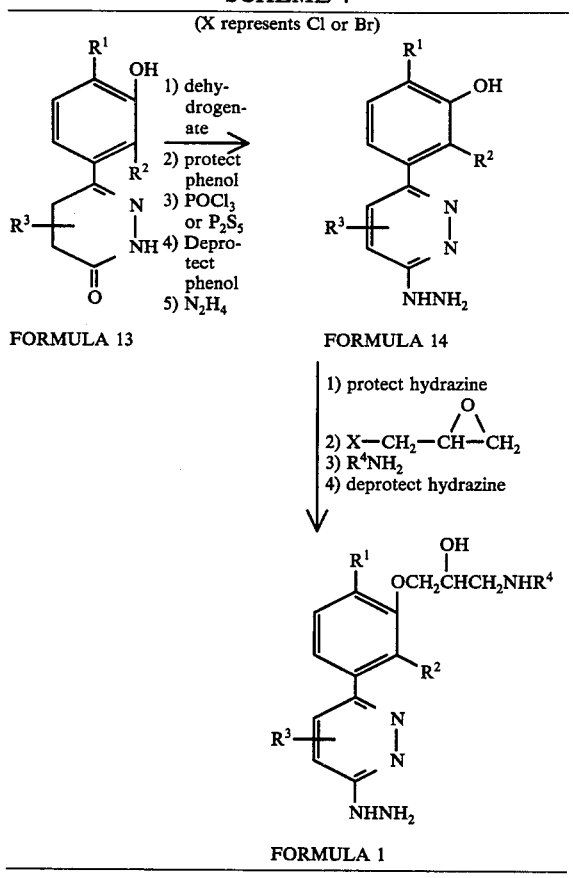

FORMULA 13

FORMULA 14

FORMULA 1

As stated above, the compounds of Formula 1 are β-adrenergic blocking agents and vasodilators. β-Adrenergic blocking agents are useful in the treatment of angina pectoris, cardiac arrhythmias and hypertension and vasodilators are often used in the treatment of hypertension. It will be appreciated that the compounds of the present invention which exhibit concomitant β-adrenergic blocking and vasodilator activity such as to cause a fall in blood pressure without tachycardia in man, are particularly useful. The β-adrenergic blocking activity of our compounds may be demonstrated in a suitable test preparation such as cats anaesthetised with pentobarbitone sodium (Nembutal), 60 mg/Kg i.p. In such anaesthetised cats, intravenous injections of isoprenaline cause tachycardia, and vasodilation in the hind-limb. These effects of isoprenaline, which are dose-dependent and are due to stimulation of β-adrenoreceptors, can be reduced or abolished by intravenous administration of from 0.01 to 100 micromoles/Kg of the β-adrenergic blocking agent of Formula 1.

Two tests may be used in the estimation of vasodilatation. In the first of these, the fall in blood pressure is measured in rats of a spontaneously hypertensive strain to which our compounds have been subcutaneously or orally administered in a concentration of from 0.1 to 1000 micromoles/Kg. Over a period of 6 hours commencing one hour before the administration of the compound the blood pressure and heart rate are monitored directly from indwelling polythene cannulae placed in the carotid artery. In the second test vasodilatation is measured directly as a decrease in vascular resistance of the autoperfused hindquarters of anaesthetised rats injected intra-arterially or intravenously with from 0.1 to 100 micromoles/Kg of a compound of Formula 1.

For therapeutic use, the pharmacologically active compounds of the present invention will normally be administered as a pharmaceutical composition comprising as the or an essential active ingredient, at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, acetic, citric and maleic acids.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Examplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25mg to about 500 mg. If a liquid carrier is used, the preparation may be in the form of a syrup, emulsion, soft gelatin capsule, sterile injectable liquid such as in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to produce β-adrenergic blockade and vasodilatation. The route of administration may be oral or parenteral.

Preferably, each dosage unit will contain the active ingredient in an amount of from about 25 mg to about 500 mg, most preferably from about 50 mg to about 250 mg.

The active ingredient will preferably by administered in equal doses one to three times per day. The daily dosage regimen will preferably be from about 100 mg to about 2 g.

Other pharmacologically active compounds may in certain cases be included in the composition. Advantageously the composition will be made up in a dosage unit form appropriate to the desired mode of administration for example as a tablet, capsule or injectable solution.

The invention is illustrated but in no way limited by the following examples, wherein all temperatures are given in degrees centigrade:

EXAMPLE 1

Preparation of 3-[3-(2-hydroxy-3-isopropylaminopropoxy)phenyl]-6-hydrazinopyridazine (i) A mixture of finely powdered 6-(3-hydroxyphenyl)-4,5-dihydro-3(2H)-pyridazinone (21.6 g, 0.11 mole), epichlorohydrin (90 ml, 1.1 mole), and piperidine (1 ml) was heated on a steam bath for 90 minutes. Evaporation of the solution under reduced pressure gave an oil which was dissolved in dichloromethane and stirred with dilute sodium hydroxide solution (60 ml). The organic phase was washed with water, dried, and evaporated under reduced pressure to a viscous oil (27 g, 96%). Purification on a silica column by eultion with chloroform gave 6-[3-(2,3-epoxypropoxy)phenyl]-4,5-dihydro-3(2H)-pyridazinone (16.5 g, 59%) as an oil which, when treated with ether, gave a white solid (13.7 g, 49%, m.p. 108°–112° C). The pure epoxide, recrystallised from methanol-petroleum ether (b.p. 60°–80° C), had m.p. 110°–112° C. (Found: C, 63.96; H, 5.70; N, 11.43; $M^+$, 246. $C_{13}H_{14}N_2O_3$ requires: C, 63.39; H, 5.73; N, 11.38%; M, 246).

(ii) A stirred mixture of 6-[3-(2,3-epoxypropoxy)phenyl]-4,5-dihydro-3(2H)-pyridazinone (10 g, 0.04 mole), methanol (100 ml), and isopropylamine (20.8 ml, 0.24 mole) was heated under reflux for 90 minutes. Evaporation of the solution under reduced pressure gave a white solid which, when treated with ether, gave crude 6-[3-(2-hydroxy-3-isopropylaminopropoxy)phenyl]-4,5-dihydro-3(2H)-pyridazinone (11.7 g, 94%, m.p. 137°–141° C). The hemisulphate, recrystallised from aqueous methanol-ether, had m.p. 256°–258° C.

(Found: C, 53.88; H, 6.67; N, 11.63; $SO_4^{--}$, 13.49; $M^+$, 305. $C_{16}H_{23}N_3O_3 \cdot \frac{1}{2}H_2SO_4$ requires: C, 54.22; H, 6.83; N, 11.86; $SO_4^{--}$, 13.55%; M (base) 305).

(iii)(a) A stirred mixture of 6-[3-(2-hydroxy-3-isopropylaminopropoxy)phenyl]-4,5-dihydro-3(2H)-pyridazinone (14.3g, 0.047 mole), acetic anhydride (75 ml), and pyridine (15 drops) was heated in a water bath at 75° C for 1 hour, then diluted with glacial acetic acid (75 ml). Bromine (8.24 g, 0.052 mole) in acetic acid (30 ml) was added dropwise during 1 hour and the mixture was stirred for an additional 20 minutes at 75° C. The mixture was evaporated under reduced pressure and the residue was dissolved in ethyl acetate and washed with dilute hydrochloric acid and with water. Evaporation of the dried solution gave an oil which was purified on a silica column by elution with mixtures of chloroform and methanol to give 6-[3-(2-acetoxy-3-N-acetylisopropylaminopropoxy)phenyl]-3(2H)-pyridazinone as a glass (12.7 g, 70%) (Found: $M^+$, 387; $C_{20}H_{25}N_3O_5$ requires: M, 387).

(b) 6-[3-(2-Hydroxy-3-isopropylaminopropoxy)phenyl]-4,5-dihydro-3(2H)-pyridazinone (2 g, 0.0065 mole) and sodium 3-nitrobenzenesulphonate (1.48 g, 0.0065 mole) were added to a solution of sodium hydroxide (0.52 g, 0.013 mole) in water (20 ml) and the stirred mixture was heated under reflux for 3 hours. The cold solution was neutralised with hydrochloric acid, and excess of potassium carbonate was added. 6-[3-(2-Hydroxy-3-isopropylaminopropoxy)phenyl]-3(2H)-pyridazinone (1.7 g, 90%, m.p. 147° C) was collected, washed with water, and recrystallised from ethyl acetate. A mixture of 6-[3-hydroxy-3-isopropylaminopropoxy)phenyl]-3(2H)-pyridazinone (1.0 g, 0.0033 mole), acetic anhydride (5 ml), and pyridine (1 drop), was heated on a steam bath for 1 hour. The mixture was evaporated, aqueous ethanol was added and the mixture was evaporated. The residue in dichloromethane was washed with dilute hydrochloric acid and with water. Evaporation of the dried solution gave 6-[3-(2-acetoxy-3-N-acetylisopropylaminopropoxy)phenyl]-3(2H)-pyridazinone as glass.

(iv) Phosphorus pentasulphide (15.5 g, 0.07 mole) was added to a stirred solution of 6-[3-acetoxy-3-N-acetylisopropylaminopropoxy)phenyl]-3(2H)-pyridazinone (9 g, 0.023 mole) in dry pyridine (175 ml) and the stirred mixture was heated under reflux for 1 hour. The solution was diluted with an equal volume of water and the residue, after evaporation under reduced pressure, was digested with a mixture of water and ethyl acetate. The organic solution was washed with dilute hydrochloric acid and with water. Evaporation of the dried solution under reduced pressure gave the crude product (7.17 g, 74%) which was purified on a silica column by elution with chloroform and methanol mixtures, to give 6-[3-(2-acetoxy-3-N-thioacetylisopropylaminopropoxy)phenyl]-3(2H)-pyridazinethione (5.01 g, 51%) as a yellow glass. (Found: $M^+$, 419. $C_{20}H_{25}N_3O_3S_2$ requires: M, 419).

(v) 6-[3-(2-Acetoxy-3-N-thioacetylisopropylaminopropoxy)phenyl]-3-(2H)-pyridazinethione (5.01 g, 0.012 mole) was added to a stirred solution of sodium hydroxide (2.88 g, 0.072 mole) in a mixture of methanol (120 ml) and water (60 ml) and the mixture was heated under reflux for 1.5 hours. The residue after evaporation under reduced pressure was dissolved in water and the mixture was adjusted to pH 9 with potassium carbonate to give a gum which slowly crystallised. 6-[3-Hydroxy-3-isopropylaminopropoxy)phenyl]-3(2H)-pyridazinethione (2.98 g, 118°–122° C) was collected and washed with water. Recrystallisation from water gave the pure thione, m.p. 125°–127° C. (Found: C, 60.10; H, 6.43; N, 13.13; $M^+$, 319) $C_{16}H_{21}N_3O_2S$ requires: C, 60.20; H, 6.63; N, 13.15%, M, 319)

(vi) A stirred mixture of 6-[3-(2-hydroxy-3-isopropylaminopropoxy)-phenyl]-3(2H)-pyridazinethione (1.27 g, 0.004 mole) and hydrazine hydrate (20 ml) was heated under reflux in an atmosphere of nitrogen for 90 minutes. Excess of hydrazine hydrate was removed by evaporation under reduced pressure to give 3-[3-(2-hydroxy-3-isopropylamino)phenyl]-6-hydrazinopyridazine which was isolated from aqueous methanol-ethanol as the sulphate salt (1.37 g, 83%, m.p. 202.5°–204.5° C) (Found: C, 45.81; H, 6.03; N, 16.56; S, 7.45 $C_{16}H_{23}N_5O_2 \cdot H_2SO_4 \cdot \frac{1}{2}H_2O$ requires: C, 45.76; H, 6.12; N, 16.68; S, 7.63%)

EXAMPLE 2

3-[3-(2-Hydroxy-3-phenylethylaminopropoxy)phenyl]-6-hydrazinopyridazine (i) 6-[3-(2,3-Epoxypropoxy)phenyl]-4,5-dihydro-3(2H)-pyridazinone was reacted with phenylethylamine in a similar manner to that described in Example 1(ii) to give 6-[3-(2-hydroxy-3-phenethylaminopropoxy)phenyl]-4,5-dihydro-3(2H)-pyridazinone.

(ii) 6-[3-(2-Hydroxy-3-phenethylaminopropoxy)phenyl]-4,5-dihydro-3(2H)-pyridazinone was subjected to a series of reactions similar to that described in Example 1 (iii(b) – vi) to give the title compound.

EXAMPLE 3

3-[3-(3-t-Butylamino-2-hydroxypropoxy)-4-methylphenyl]-6-hydazinopyridazine (i) A stirred suspension of 3-(3-hydroxy-4-methylbenzoyl)propionic acid (6.75 g, 0.032 mole) in water (40 ml) was treated with hydrazine hydrate (2.4 ml, 0.048 mole) and heated under reflux for one hour. The mixture was diluted with water (50 ml) and cooled. The product (6.36 g, 96%, m.p. 215°–218° C) was collected, washed with water and crystallised from ethanol to give pure 6-(3-hydroxy-4-methylphenyl)-4,5-dihydro-3(2H)-pyridazinone, m.p. 216°–218° C. (Found: C, 64.80; H, 5.94; N, 13.52; M+, 204. $C_{11}H_{12}N_2O_2$ requires: C, 64.69; H, 5.92; N, 13.72%; M, 204).

(ii) A mixture of powdered 6-(3-hydroxy-4-methylphenyl)-4,5-dihydro-3(2H)-pyridazinone (5.0 g, 0.024 mole), epichlorohydrin (19.3 ml, 0.24 mole), and piperidine (0.2 ml) was heated on a steam bath for one hour. Evaporation of the solution under reduced pressure gave an oil which was dissolved in a small volume of dichloromethane and stirred with dilute sodium hydroxide solution (15 ml). The organic phase was washed with water, dried and evaporated to an oil which under reduced pressure gave a solid (6.2 g, 98%). Trituration with ethanol-ether gave crude 6-[3-(2,3-epoxypropoxy)-4-methylphenyl]-4,5-dihydro-3(2H)-pyridazinone (4.81 g, 76% m.p. 128°–132° C). Purification, either by recrystallisation from ethanol, or in chloroform on silica gave the pure epoxide, m.p. 140°–142.5° C. (Found: C, 64.69; H, 6.26; N, 10.70; M+, 260. $C_{14}H_{15}N_2O_3$ requires: C, 64.60; H, 6.20; N, 10.76%; M, 260).

(iii) A stirred mixture of 6-[3-(2,3-epoxypropoxy)-4-methylphenyl]-4,5-dihydro-3(2H)-pyridazinone (3.3 g, 0.013 mole), methanol (33 ml) and t-butylamine (8 ml, 0.076 mole) was heated under reflux for 75 minutes. Evaporation of the solution under reduced pressure gave a gum which solidified when treated with ether. 6-[3-(3-t-Butylamino-2-hydroxpropoxy)-4-methylphenyl]-4,5-dihydro-3(2H)-pyridazinone (4.27 g, 100%, m.p. 153°–158° C) was purified as its hemisulphate, m.p. 275°–277° C (decomposition), after recrystallisation from aqueous ethanol. (Found: C, 56.51; H, 7.35; N, 10.83; $SO_4^{--}$, 12.84; M+, 333. $C_{18}H_{27}N_3O_3.\frac{1}{2}H_2SO_4$ requires: C, 56.53; H, 7.38; N, 10.98; $SO_4^{--}$, 12.55%; M (base), 333).

(iv) A stirred mixture of 6-[3-(3-t-Butylamino-2-hydroxypropoxy)-4-methylphenyl]-4,5-dihydro-3(2H)-pyridazinone (16.05 g, 0.048 mole), acetic anhydride (160 ml) and potassium carbonate (17.91 g, 0.13 mole) was heated in a 75° water bath. Heating was continued for 120 minutes, acetic acid (160 ml) was added, followed by bromine (7.8 g, 0.048 mole) in acetic acid (160 ml) added dropwise during 90 minutes, and the mixture was heated for an additional 20 minutes. The residue after evaporation was dissolved in dichloromethane and washed with water. Evaporation of the dried organic solution gave a glass which was purified on a silica column by elution with mixtures of chloroform and methanol to give 6-[3-(2-acetoxy-3-N-acetyl-t-butylaminopropoxy)-4-methylphenyl]-3(2H)-pyridazinone (15.0 g, 75%, softening point 157°–160°) obtained as a glassy foam by evaporation under reduced pressure.

6-[3-(2-acetoxy-3-N-acetyl-t-butylaminopropoxy)-4-methylphenyl]-3(2H)-pyridazinone (14.6 g, 0.035 mole) in dry pyridine (280 ml) was treated with phosphorus pentasulphide (20.8 g, 0.094 mole) in a similar manner to that described in Example 1(iv) to give 6-[3-(2-acetoxy-3-N-acetyl-t-butylaminopropoxy)-4-methylphenyl]-3(2H)-pyridazinethione which was crystallised from methanol (10.5 g, 69%; m.p. 160°)

(vi) 6-[3-(2-acetoxy-3-N-acetyl-t-butylaminopropoxy)-4-methylphenyl]-3(2H)-pyridazinethione (10.6 g, 0.024 mole) was hydrolysed in a solution of sodium hydroxide (1N, 94.7 ml) in methanol (142 ml) in a manner similar to that described in Example 1 (iv) to give 6-[3-(3-t-butylamino-2-hydroxypropoxy)-4-methylphenyl]-3(2H)-pyridazinethione which was crystallised from 2-methoxyethanol (4.5 g, 52%, m.p. 218°) (Found: C, 61.43; H, 7.21; N, 11.83 $C_{18}H_{25}N_3O_2S.\frac{1}{4}H_2O$ requires: C, 61.42; H, 7.30; N, 11.94%)

(vii) A stirred mixture of 6-[3-(3-t-butylamino-2-hydroxypropoxy)-4-methylphenyl]-3(2H)-pyridazinethione (1.9 g, 0.00547 mole) and hydrazine hydrate (40 ml) was heated under reflux in an atmosphere of nitrogen for 180 minutes. The cooled mixture was diluted with water (40 ml) and extracted with dichloromethane. The organic layer was washed twice with water (5 ml) then treated with sulphuric acid (1N, 5.2 ml). Treatment of the residue, after evaporation of the dichloromethane, with ethanol gave 3-[(3-t-butylamino-2-hydroxypropoxy)-4-methylphenyl]-6-hydrazinopyridazine (1.5 g, 79%, m.p. 145°–155° (d)).

EXAMPLE 4

3-[3-(3-t-Butylamino-2-hydroxypropoxy)-4-fluorophenyl]-6-hydrazinopyridazine (i) 3-(4-Fluorobenzoyl)propionic acid (250 g, 1.28 mole) was added in portions to stirred fuming nitric acid (1000 ml) maintained at −15° C, the mixture was stirred an additional 30 minutes and then poured into ice-water (3000 ml). The product was collected, washed with water, and recrystallised from propanol to give 3-(4-fluoro-3-nitrobenzoyl)propionic acid (175 g, 56%, m.p. 136° C). (Found: C, 49.98; H, 3.34; N, 5.69. $C_{10}H_8FNO_5$ requires: C, 49.80; H, 3.34; N, 5.81%)

(ii) A stirred mixture of 3-(4-fluoro-3-nitrobenzoyl)propionic acid, cyclohexene, palladium on charcoal, and ethanol, was heated under reflux for 18 hours. Evaporation of the filtered solution gave 3-(3-amino-4-fluorobenzoyl)propionic acid.

(iii) 3-(3-amino-4-fluorobenzoyl)propionic acid was diazotised in sulphuric acid solution with sodium nitrite and the diazonium salt solution was added dropwise to boiling aqueous sulphuric acid to give 3-(4-fluoro-3-hydroxybenzoyl)propionic acid.

(iv) 3-(4-Fluoro-3-hydroxybenzoyl)propionic acid was cyclised with hydrazone hydrate in a similar manner to that described in Example 3 (i) to give 6-(4-fluoro-3-hydroxyphenyl)-4,5-dihydro-3(2H)-pyridazinone.

(v) 6-(4-Fluoro-3-hydroxyphenyl)-4,5-dihydro-3(2H)-pyridazinone was subjected to a series of reactions similar to that described in Examples 1 and 3 to give the title compound.

EXAMPLE 5

3-[3-(3-t-Butylamino-2-hydroxypropoxy)-4-chlorophenyl]-6-hydrazinopyridazine (i) 3-(3-amino-4-chlorobenzoyl)propionic acid was diagotised in sulphuric acid solution with sodium nitrite and the diazonium salt solution was added dropwise to boiling aqueous sulphuric acid to give 3-(4-chloro-3-hydroxybenzoyl)propionic acid.

(ii) 3-(4-chloro-3-hydroxybenzoyl)propionic acid was cyclised with hydrazine hydrate in a similar manner to that described in Example 3 (i) to give 6-(4-chloro-3-hydroxyphenyl)-4,5-dihydro-3(2H)-pyridazinone.

(iii) 6-(4-chloro-3-hydroxyphenyl)-4,5-dihydro-3(2H)-pyridazinone was subjected to a series of reactions similar to that described in Examples 1 and 3 to give the title compound.

EXAMPLE 6

3-[4-Bromo-3-(3-t-butylamino-2-hydroxypropoxy)-phenyl]-6-hydrazinopyridazine (i) 3-(4-Bromobenzoyl)propionic acid was added in portions to well stirred fuming nitric acid at −15° C and the resultant mixture stirred a further 30 minutes then poured into ice-water to give 3-(4-bromo-3-nitrobenzoyl)propionic acid.

(ii) A solution of 3-(4-bromo-3-nitrobenzoyl)propionic acid in ethanol was treated with ion filings and aqueous hydrobromic acid. The residue after evaporation under reduced pressure was treated with water to give 3-(3-amino-4-bromobenzoyl)-propionic acid.

(iii) By subjecting 3-(3-amino-4-bromobenzoyl)propionic acid to a series of reactions similar to that described in Example 5, the title compound may be prepared.

EXAMPLE 7

3-[3-(3-t-Butylamino-2-hydroxypropoxy)-4-nitrophenyl]-6-hydrazinopyridazine (i) 3-(3-Hydroxybenzoyl)propionic acid was added in portions to well stirred fuming nitric acid at −15° C. The resultant mixture was stirred a further 10 minutes in the cold then poured into ice-water. The crude product was triturated with methanol to give 3-(3-hydroxy-4-nitrobenzoyl)propionic acid, which after recrystallisation from water had m.p. 158° − 160.3° C (Found: C, 50.25; H, 3.75; N, 5.88; M+, 239 $C_{10}H_9NO_6$ requires: C, 50.21; H, 3.79; N, 5.86%; M, 239)

(ii) 3-(3-Hydroxy-4-nitrobenzoyl)propionic acid was cyclised with an equimolar amount of hydrazine hydrate in a similar manner to that described in Example 3(i) to give 6-(3-hydroxy-4-nitrophenyl)-4,5-dihydro-3(2H)-pyridazinone.

(iii) 6-(3-Hydroxy-4-nitrophenyl)-4,5-dihydro-3(2H)-pyridazinone was subjected to a series of reactions similar to that described in Examples 1 and 3 to give the title compound.

EXAMPLE 8

3-[4-Amino-3-(3-t-butylamino-2-hydroxypropoxy)-phenyl]-6-hydrazinopyridazine (i) A solution of 6-[3-(3-t-butylamino-2-hydroxypropoxy)-4-nitrophenyl]-4,5-dihydro-3(2H)-pyridazinone in ethanol was heated under reflux with palladium on charcoal and excess of cyclohexene for 18 hours. Evaporation of the filtered solution under reduced pressure gave 6-[4-amino-3-(3-t-butylamino-2-hydroxypropoxy)phenyl]-4,5-dihydro-3(2H)-pyridazinone.

(ii) By subjecting 6-[4-amino-3-(3-t-butylamino-2-hydroxypropoxy)-phenyl]-4,5-dihydro-3-(2H)-pyridazinone to a series of reactions similar to that described in Examples 1 and 3, the title compound may be prepared.

EXAMPLE 9

3-[3-(3-t-Butylamino-2-hydroxypropoxy)-4-cyanophenyl]-6-hydrazinopyridazine (i) 3-(3-Hydroxy-4-nitrobenzoyl)propionic acid in ammonium hydroxide solution was reduced with ferrous sulphate to give 3-(4-amino-3-hydroxybenzoyl)-propionic acid.

(ii) 3-(4-Amino-3-hydroxybenzoyl)propionic acid was diazotised in dilute hydrochloric acid with sodium nitrite and the neutralised solution was treated with cuprous cyanide to give 3-(4-cyano-3-hydroxybenzoyl)-propionic acid.

(iii) 3-(4-Cyano-3-hydroxybenzoyl)propionic acid was cyclised with hydrazine hydrate in a similar manner to that described in Example 3 (i) to give 6-(4-cyano-3-hydroxyphenyl)-4,5-dihydro-3(2H)-pyridazinone (iv) 6-(4-Cyano-3-hydroxyphenyl)-4,5-dihydro-3(2H)-pyridazinone was subjected to a series of reactions similar to that described in Examples 1 and 3 to give the title compound.

EXAMPLE 10

3-[3-(3-t-Butylamino-2-hydroxypropoxy)-4-hydroxymethylphenyl]-6-hydrazinopyridazine (i) To a solution of methyl 3-(3-hydroxybenzoyl)propionate in chloroform at −5° to 0° was added paraformaldehyde and zinc chloride. Dry hydrogen chloride was passed through the well-stirred solution until the saturation point was reached and the stirring was continued for a further hour at room temperature. The reaction mixture was then poured into ice-water, the product extracted into dichloromethane and the organic layer washed with water and dried over magnesium sulphate. Evaporation of the dichloromethane gave an oily residue from which methyl 3-(4-chloromethyl-3-hydroxybenzoyl)-propionate was obtained by crystallisation from ethanol.

(ii) A mixture of methyl 3-(4-chloromethyl-3-hydroxybenzoyl)-propionate and 3N potassium hydroxide solution was heated under reflux for 4 hours to give 3-(3-hydroxy-4-hydroxymethylbenzoyl)propionic acid.

(iii) 3-(3-Hydroxy-4-hydroxymethylbenzoyl)propionic acid was cyclised with hydrazine hydrate in a similar manner to that described in Example 3(i) to give 6-(3-hydroxy-4-hydroxymethylphenyl)-4,5-dihydro-3(2H)-pyridazinone.

(iv) 6-(3-Hydroxy-4-hydroxymethylphenyl)-4,5-dihydro-3(2H)-pyridazinone was subjected to a sequence of reactions similar those described in Example 1 (iiib) and 3 (ii, iii and v) to give 6-[3-(2-acetoxy-3-N-acetyl-t-butylamino)-4-acetoxymethylphenyl]-3(2H)-pyridazinethione.

(v) 6-[3-(2-Acetoxy-3-N-acetyl-t-butylamino)-4-acetoxymethylphenyl]-3(2H)-pyridazinethione was subjected to a sequence of reactions similar to those described in Example 1 (v and vi) to give 3-[3-(3-t-butylamino-2-hydroxypropoxy)-4-hydroxymethylphenyl]-6-hydrazinopyridazine which was converted into its sulphate salt.

EXAMPLE 11

3-[2-Hydroxy-3-(2-hydroxy-3-isopropylaminopropoxy)phenyl]-6-hydrazinopyridazine (i) 3-(2,3-Dihydroxybenzoyl)propionic acid was cyclised with hydrazine hydrate in a similar manner to that described in Example 3 (i) to give 6-(2,3-dihydroxyphenyl)-4,5-dihydro-3(2H)-pyridazinone.

(ii) 6-(2,3-Dihydroxyphenyl)-4,5-dihydro-3(2H)-pyridazinone was reacted with 5-chloromethyl-3-isopropyl-2-phenyloxazolidine in the presence of sodium methoxide to give 6-[2-hydroxy-3-(3-isopropyl-2-phenyl-5-oxazolidinylmethoxy)phenyl]-4,5-dihydro-3(2H)-pyridazinone.

(iii) 6-[2-Hydroxy-3-(3-isopropyl-2-phenyl-5-oxazolidinylmethoxy)-phenyl]-4,5-dihydro-3(2H)-pyridazinone was dehydrogenated by a method similar to that described in Example 1 (iiib) to give 6-[2-hydroxy-3-(3-isopropyl-2-phenyl-5-oxazolidinylmethoxy)-phenyl]-3(2H)-pyridazinone.

(iv) The product from (iii) was heated in a steam bath for 1 hour with 10% aqueous hydrochloric acid to give 6-[2-hydroxy-3-(2-hydroxy-3-isopropylaminopropoxy)-phenyl]-3(2H)-pyridazinone, which was acetylated with acetic anhydride containing a trace of pyridine to give 6-[2-acetoxy-3-(2-acetoxy-3-N-acetylisopropylaminopropoxy)phenyl]-3(2H)-pyridazinone.

(v) 6-[2-acetoxy-3-(2-acetoxy-3-N-acetylisopropylaminopropoxy)-phenyl]-3-(2H)-pyridazinone was subjected to a series of reactions similar to that described in Example 1 (iv-vi) to give the title compound.

EXAMPLE 12

3-[3-(3-t-Butylamino-2-hydroxypropoxy)-2-methoxyphenyl]-6-hydrazinopyridazine (i) A solution of 2,3-dimethoxylithiobenzene in tetrahydrofuran was added dropwise to a cold stirred solution of N-methylsuccinimide in benzene. The mixture was stirred overnight at room temperature, then treated with ammonium chloride solution and extracted with chloroform. The washed and dried extract was evaporated to low volume to give a mixture of the tautomers N-methyl 3-(2,3-dimethoxybenzoyl)propionamide and N-methyl 2-(2,3-dimethoxyphenyl)-2-hydroxy-5-pyrrolidinone.

(ii) This product was boiled with 55% hydriodic acid and the mixture poured into water to give 3-(2,3-dihydroxybenzoyl)propionic acid, which was esterified with sulphuric acid in methanol to give methyl 3-(2,3-dimethoxybenzoyl)propionate.

(iii) Methyl 3-(2,3-dihydroxybenzoyl)propionate was treated with boroacetic anhydride in acetic anhydride on a steam bath for 20 minutes and the mixture was poured into water and stirred for 2 hours to give methyl 3-(3-acetoxy-2-hydroxybenzoyl)-propionate.

(iv) A stirred mixture of methyl 3-(3-acetoxy-2-hydroxybenzoyl)-propionate, potassium carbonate, methyl iodide, and dry acetone, was heated under reflux for 24 hours. Evaporation of the filtered solution gave methyl 3-(3-acetoxy-2-methoxybenzoyl)-propionate.

(v) Methyl 3-(3-acetoxy-2-methoxybenzoyl)propionate was warmed on a steam bath with dilute sodium hydroxide solution, and the resultant solution was acidified with hydrochloric acid to give 3-(3-hydroxy-2-methoxybenzoyl)propionic acid.

(vi) 3-(3-hydroxy-2-methoxybenzoyl)propionic acid was cyclised with hydrazine hydrate in a similar manner to that described in Example 3 (i) to give 6-(3-hydroxy-2-methoxyphenyl)-4,5-dihydro-3(2H)-pyridazinone.

(vii) 6-(3-hydroxy-2-methoxyphenyl)-4,5-dihydro-3(2H)-pyridazinone was subjected to series of reactions similar to that described in Examples 1 and 3 to give the title compound.

EXAMPLE 13

3-[3-(3-t-Butylamino-2-hydroxypropoxy)-2-methylphenyl]-6-hydrazinopyridazine (i) Crude 3-(5-t-butyl-2-methylbenzoyl)propionic acid was added in portions to a well stirred mixture of fuming nitric acid and sulphuric acid at −15° C. After the addition, the mixture was stirred for a further 10 minutes then poured into ice-water. Crude 3-(5-t-butyl-2-methyl-3-nitrobenzoyl)propionic acid was collected and washed with water.

(ii) The product from (i) above was stirred with aluminum chloride in an excess of benzene until transalkylation was complete. The mixture was hydrolysed with ice - hydrochloric acid and the acidic product purified to give 3-(2-methyl-3-nitrobenzoyl)-propionic acid.

(iii) 3-(2-methyl-3-nitrobenzoyl)propionic acid in ammonium hydroxide solution was reduced with ferrous sulphate to give 3-(3-amino-2-methylbenzoyl)propionic acid.

(iv) 3-(3-amino-2-methylbenzoyl)propionic acid was diazotised in a solution of sulphuric acid with sodium nitrite, and the diazonium salt solution was added dropwise to boiling aqueous sulphuric acid to give 3-(3-hydroxy-2-methylbenzoyl)proprionic acid.

(v) 3-(3-hydroxy-2-methylbenzoyl)propionic acid was cydised with hydrazine hydrate in a similar manner to that described in Example 3 (i) to give 6-(3-hydroxy-2-methylphenyl)-4,5-dihydro-3(2H)-pyridazinone.

(vi) By subjecting 6-(3-hydroxy-2-methylphenyl)-4,5-dihydro-3(2H)-pyridazinone to a series of reactions similar to those described in Examples 1 and 3, the title compound may be prepared.

EXAMPLE 14

3-[3-(3-t-Butylamino-2-hydroxypropoxy)-2-chlorophenyl]-6-hydrazinopyridazine (i) A solution of redistilled acrylonitrile (20 g, 0.375 mole) in dimethylformamide (100 ml) was added dropwise to a stirred solution of 3-acetoxy-2-chlorobenzaldehyde (99.2 g, 0.5 mole) and sodium cyanide (12.25 g, 0.25 mole) in dimethylformamide (250 ml) at 35° C during 30 minutes. The mixture was stirred at 35° C for 4 hours, then poured into twice its own volume of water and the mixture was extracted with chloroform. The washed and dried extract was evaporated to give 3-(3-acetoxy-2-chlorobenzoyl)propionitrile.

(ii) 3-(3-acetoxy-2-chlorobenzoyl)propionitrile was subjected to acid hydrolysis to give 3-(2-chloro-3-hydroxybenzoyl)propionic acid.

(iii) 3-(2-chloro-3-hydroxybenzoyl)propionic acid was cyclised with hydrazine hydrate in a similar manner to that described in Example 3(i) to give 6-(2-chloro-3-hydroxyphenyl)-4,5-dihydro-3(2H)-pyridazinone.

(iv) By subjecting 6-(2-chloro-3-hydroxyphenyl)-4,5-dihydro-3(2H)-pyridazinone to a series of reactions similar to those described in Examples 1 and 3, the title compound may be prepared.

EXAMPLE 15

3-[3-(2-Hydroxy-3-isopropylamino)phenyl]-4-methyl-6-hydrazinopyridazine (i) 3-Acetoxybenzaldehyde was treated with sodium cyanide and crotononitrile in dimethylformamide in a similar manner to that described in Example 14(i) to give 3-(3-acetoxybenzoyl)-butyronitrile.

(ii) 3-(3-Acetoxybenzoyl)butyronitrile was subjected to a sequence of reactions similar to those described in Example 14 (ii and iii) to give 6-(3-hydroxyphenyl)-4,5-dihydro-5-methyl-3(2H)-pyridazinone.

(iii) 6-(3-Hydroxyphenyl)-4,5-dihydro-5-methyl-3(2H)pyridazinone was subjected to a sequence of reactions similar to those described in Example 1 to give 3-[3-(2-hydroxy-3-isopropylamino)-phenyl]-4-methyl-6-hydrazinopyridazine.

EXAMPLE 16

| Ingredients | Amounts |
|---|---|
| 3-[3-(3-t-Butylamino-2-hydroxypropoxy)-4-methylphenyl]-6-hydrazino-pyridazine hemisulphate | 75 mg |
| Sucrose | 40 mg |
| Starch | 15 mg |
| Talc | 3 mg |
| Stearic Acid | 1 mg |

The ingredients are screened, mixed and filled into a hard gelatin capsule.

EXAMPLE 17

| Ingredients | Amounts |
|---|---|
| 3-[3-(3-t-Butylamino-2-hydroxypropoxy)-4-methylphenyl]-6-hydrazino-pyridazine hemisulphate | 100 mg |
| Lactose | 50 mg |

The ingredients are screened, mixed and filled into a hard gelatin capsule.

What is claimed is:

1. A compound of the formula

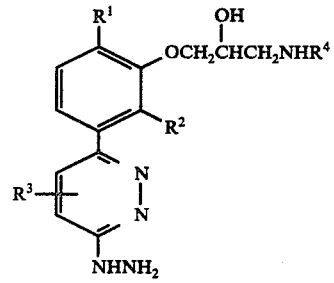

wherein $R^1$ or $R^2$ is hydrogen, the other group being hydrogen, methyl, fluoro, chloro, bromo, hydroxy, methoxy, hydroxymethyl, cyano, nitro or amino;
$R^3$ is hydrogen or methyl; and
$R^4$ is isopropyl, tertiary butyl or phenylethyl; or a pharmaceutically acceptable salt thereof.

2. A compound according to claim 1 wherein $R^1$ or $R^2$ is hydrogen, the other group being hydrogen, methyl, fluoro, chloro, hydroxy, methoxy or cyano.

3. A compound according to claim 2 wherein $R^2$ is hydrogen and $R^1$ is methyl, fluoro, methoxy or cyano.

4. A compound according to claim 1 wherein $R^1$ is hydrogen and $R^2$ is fluoro, chloro or cyano.

5. A compound according to claim 1 wherein $R^4$ is isopropyl or tertiary butyl.

6. A compound according to claim 2, said compound being 3-[3-(3-t-butylamino-2-hydroxypropoxy)phenyl]-6-hydrazinopyridazine or a pharmaceutically acceptable salt thereof.

7. A compound according to claim 3, said compound being 3-[3-(3-t-butylamino-2-hydroxypropoxy)-4-methylphenyl]-6-hydrazinopyridazine or a pharmaceutically acceptable salt thereof.

8. A compound according to claim 3, said compound being 3-[3-(3-butylamino-2-hydroxypropoxy)-4-cyanophenyl]-6-hydrazinopyridazine or a pharmaceutically acceptable salt thereof.

9. A compound according to claim 3, said compound being 3-[3-(3-t-butylamino-2-hydroxypropoxy)-4-fluorophenyl]-6-hydrazinopyridazine or a pharmaceutically acceptable salt thereof.

10. A compound according to claim 1 in the S-absolute configuration.

11. A pharmaceutical composition to concomitantly inhibit β-adrenergic receptors and produce vasodilatation comprising in an effective amount to inhibit said receptors and produce vasodilatation a compound of claim 1 in combination with a pharmaceutically acceptable diluent or carrier.

12. A method of concomitantly inhibiting β-adrenergic receptors and producing vasodilatation which comprises administering a compound of claim 1 internally to an animal in need thereof in an amount sufficient to block said receptors and produce vasodilatation.

* * * * *